US00PP20728P3

(12) United States Plant Patent
Skelton

(10) Patent No.: US PP20,728 P3
(45) Date of Patent: Feb. 9, 2010

(54) *ACTINIDIA CHINENSIS* PLANT NAMED 'X60'
(50) Latin Name: *Actinidia chinensis*
Varietal Denomination: X60

(76) Inventor: Donald Skelton, R D 1, Huntly (NZ)

( * ) Notice: Subject to any disclaimer, the term of this patent is extended or adjusted under 35 U.S.C. 154(b) by 0 days.

(21) Appl. No.: 12/072,482

(22) Filed: Feb. 26, 2008

(65) Prior Publication Data

US 2009/0217430 P1 Aug. 27, 2009

(51) Int. Cl.
*A01H 5/00* (2006.01)

(52) U.S. Cl. ..... Plt./156
(58) Field of Classification Search ..... Plt./156
See application file for complete search history.

*Primary Examiner*—June Hwu

(57) ABSTRACT

A new and distinct *Actinidia chinensis* cultivar named 'X60' is disclosed, characterized by having distinctive yellow flesh fruit, moderate cropping and a seasonal harvest time of late March. Additionally, the new variety produces fruit with very soft, slight pubescence and with a distinctive blunt stylar end shape and square shoulders. The new variety is suitable for commercial production of kiwi fruit.

3 Drawing Sheets

Latin name of the genus and species: *Actinidia chinensis.*

Variety denomination: 'X60'.

BACKGROUND OF THE INVENTION

The new cultivar is a product of a planned breeding program, begun in 1975 under the direction of the inventor, Donald Alfred Skelton, a citizen of New Zealand. The seed parent is the unpatented, proprietary seedling variety referred to as *Actinidia chinensis* 'A124' The pollen parent is the unpatented, proprietary seedling variety referred to as *Actinidia chinensis* 'RY.'

Fruit of the new variety was first evaluated in 1999 with favorable results. After the first evaluation, semi-hardwood cuttings were made of 'X60' and were grafted onto 5 seedling rootstocks 3; of *A. chinensis* and 2 of A. *deliciosa*. Evaluation, asexual propagation and grafting all first took place at the inventor's commercial nursery in Rangiriri, New Zealand in 1999. Subsequent evaluations of the variety have shown the characteristics to be true to type.

SUMMARY OF THE INVENTION

The cultivar 'X60' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'X60' These characteristics in combination distinguish 'X60' as a new and distinct *Actinidia chinensis* cultivar:

1. Distinctive yellow flesh fruit
2. Moderate cropping
3. Seasonal harvest time of late-March
4. Very soft, downy pubescence that does not adhere strongly to fruit skin.
5. Fruit with a distinctive blunt stylar end shape and square shoulders.

COMPARISON TO PARENT

Plants of the new cultivar 'X60' are similar to plants of the seed parent, *Actinidia chinensis* 'A124' in most horticultural characteristics, however, plants of the new cultivar 'X60' produce fruit that is smaller and of a different shape than the seed parent variety. Additionally, fruit of the new variety 'X60' reaches maturity two to three weeks later than 'A124.'

Plants of the new cultivar 'X60' are similar to plants of the pollen parent, *Actinidia chinensis* 'RY' in most horticultural characteristics, however, plants of the new cultivar 'X60' produce significantly more female flowers than the male parent. Whereas the new cultivar produces large quantities of female flowers, the male parent produces almost no viable female flowers.

COMMERCIAL COMPARISON

The new variety is best compared to the commercial variety, 'Hort16A,' U.S. Plant Pat. No. 11,066. 'X60' is similar to 'Hort16A' in many horticultural characteristics, however, 'X60' produces mature fruit six to 8 weeks earlier than 'Horti16A.' Additionally, the new variety produces an oblong shaped fruit, compared to ovoid. Fruit of the new variety 'X60' are distinctively blunt on the stylar end, compared to the strong pointed stylar end shape of 'Hort16A.' Fruit shape differences can also be noted in the shoulder shape. Whereas 'X60' produces fruit with strongly squared shoulder, 'Hort16A' fruit have rounded shoulders.

BRIEF DESCRIPTION OF THE PHOTOGRAPH

The accompanying photograph in FIG. 1 illustrates in full color typical foliage and flowers on plants of 'X60.'

Figure 1:
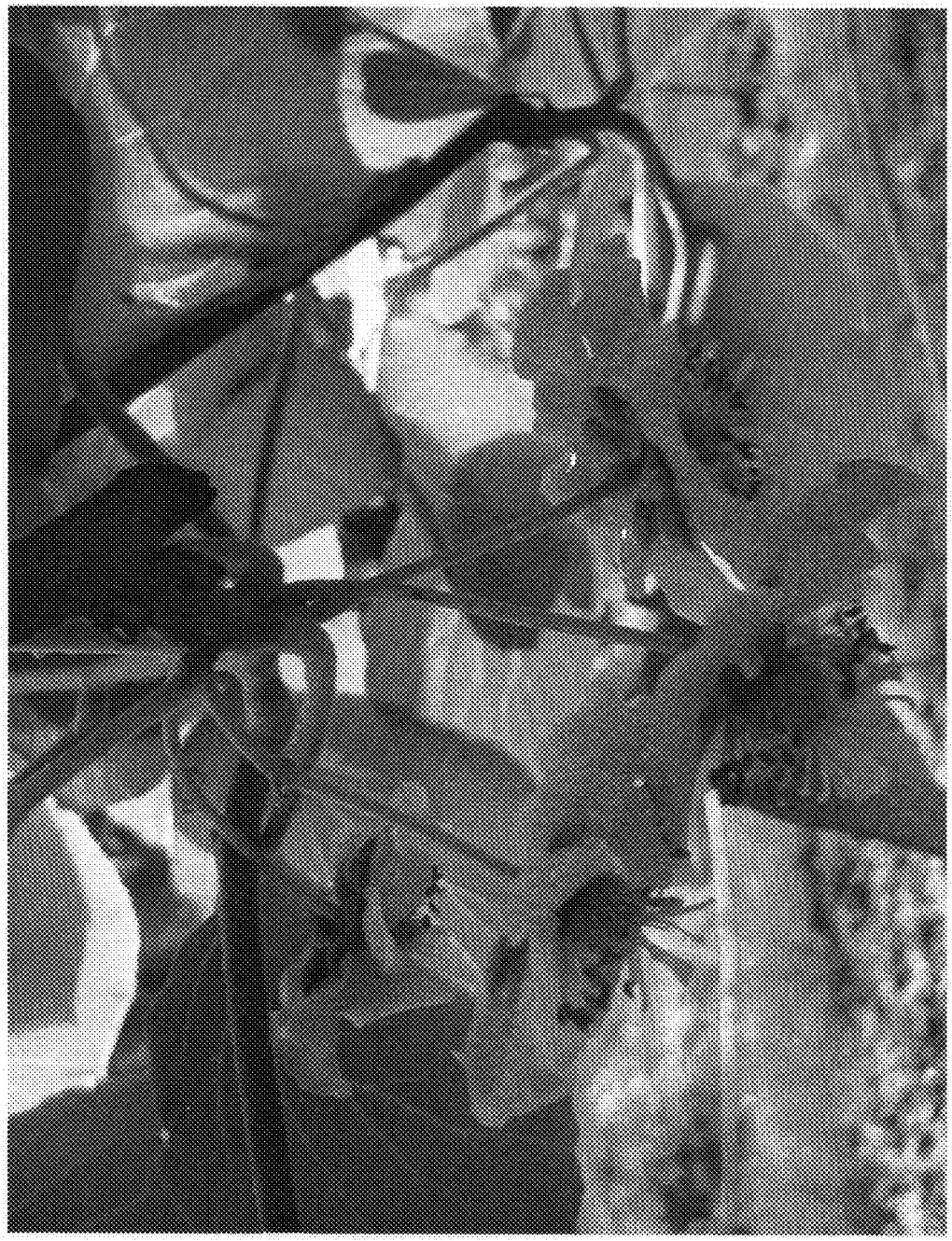
Figure 2:
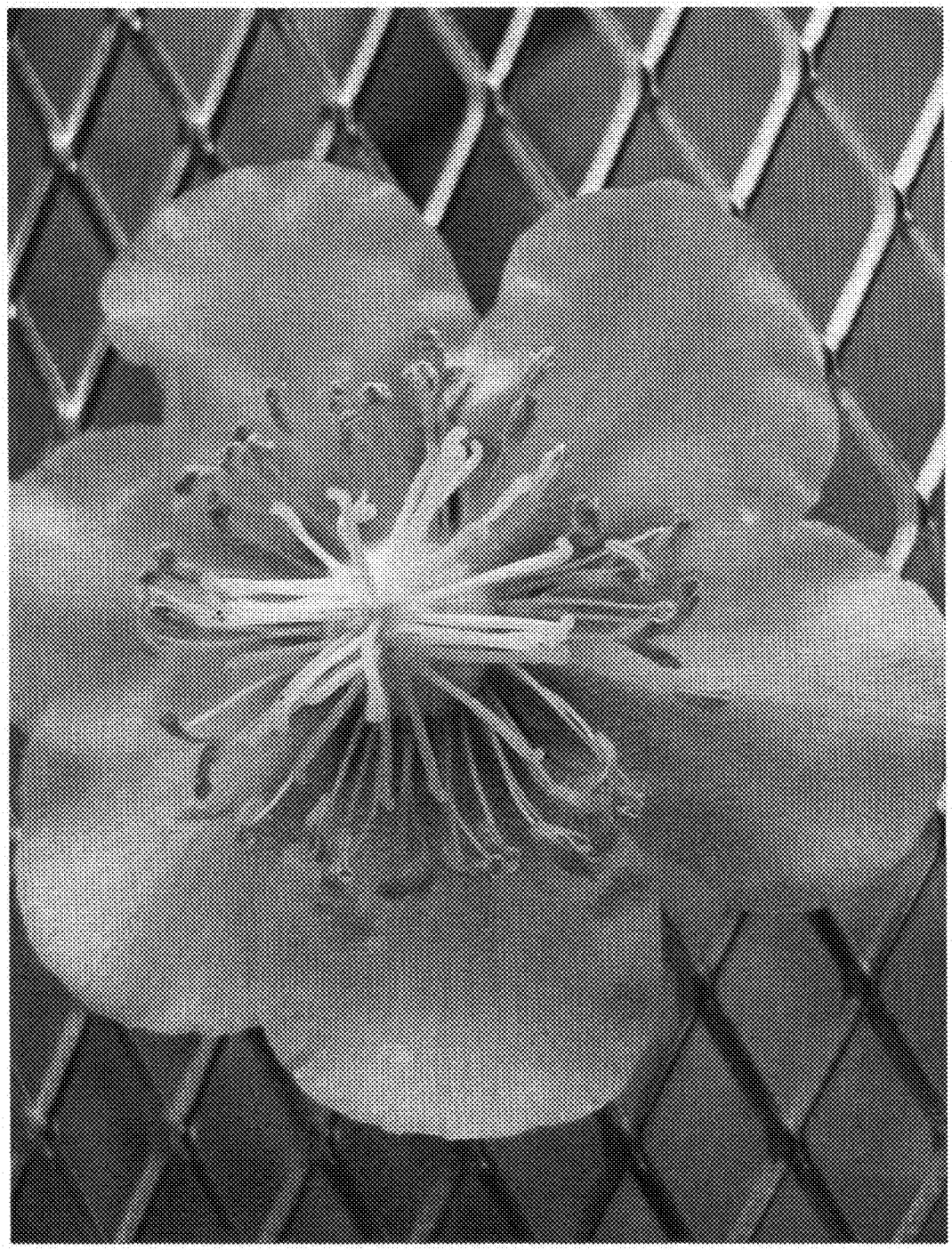
FIG. 2 illustrates in full color a typical flower of 'X60.'
Figure 3:
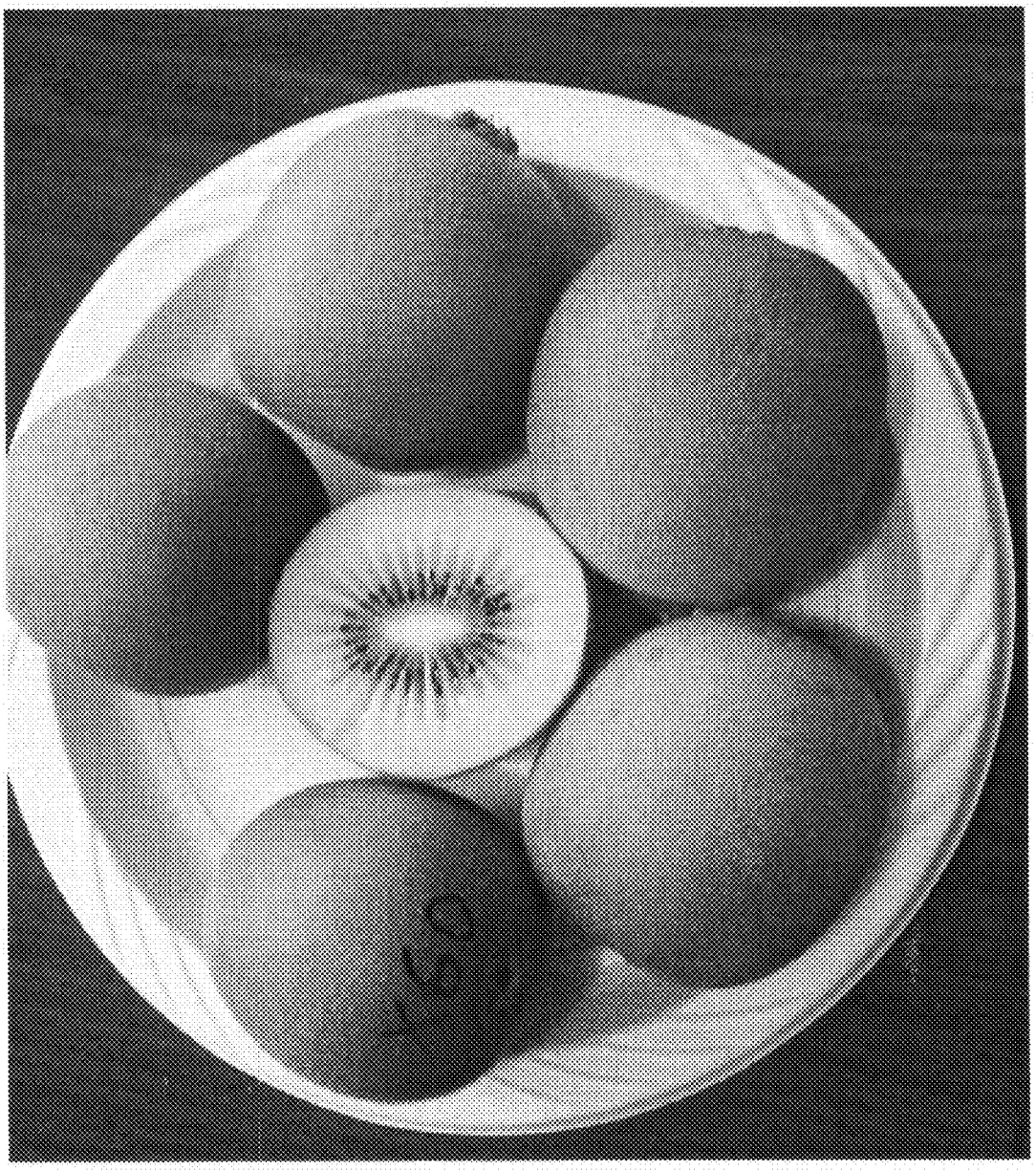
FIG. 3 shows examples of typical fruit harvested from 'X60.'

All photos were taken of plants approximately 9 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'X60' plants grown under outdoor commercial trial conditions in Rangiriri New Zealand. The growing temperature ranged from 10° C. to 25° C. with no precipitation. Measurements and numerical values represent averages of typical plant types.

Botanical classification: *Actinidia chinensis* 'X60.'

PROPAGATION

'X60' can be successfully grafted onto rootstocks of *Actnidia chinensis* or *Actinidia deliciosa.*

PLANT

*Age of the plant described.*—Approximately 9 years.
*Sex expression.*—Female.
*Ploidy.*—Diploid.
*Vigor.*—Moderate. On a scale of 1 to 10 with 10 being the highest 'X60' is a comparative 4 among commercial *Actinidia* varieties.
*Young shoot color.*—Near RHS Green 137C.
*Young shoot texture.*—Smooth, non-pubescent and no visible lenticels.
*Stem diameter.*—Average 1 cm.
*Stem texture.*—Rough.
*Trunk diameter.*—Average 3.5 cm on a 9 year old plant.
*Stem Lenticels.*—Stem lenticels either not present or barely visible to the eye.

FOLIAGE

Leaf:
*Average length.*—Range between 14–16.5 cm.
*Average width.*—Range between 15.6–19.3 cm.
*Shape of blade.*—Very broadly ovate.
*Apex.*—Rounded.
*Base.*—Cordate, not overlapping.
*Attachment.*—Petioled.
*Margin.*—Ciliate.
*Texture of top surface.*—Moderately puckered, non-pubescent.
*Texture of under side.*—Moderately glossy, non-pubescent.
*Color.*—Mature foliage upper side: Near RHS Green 137A. Mature foliage under side: Near RHS Yellow-Green 144A.
*Petiole.*—Length: Range between 14.8–16.3 cm. Pubescence: None. Other characteristics: Moderate anthocyanin on upperside of petiole. Color: Near RHS Yellow-Green 144C with a flush of Greyed-Red 181A on upperside of petiole.

FLOWER

*Bud break.*—Early September.
*Flowers per inflorescence.*—Most often 3 or 4.
*Bud color.*—Near RHS Yellow-Green 144C.
*First flower.*—Mid October.
*Diameter.*—Average 4.1 cm.
*Petal quantity.*—6 or 7 per flower.
*Petals overlapping.*—Yes.
*Color.*—Near RHS White 155A.
*Style color.*—Near RHS White 155A.
*Style quantity.*—Average 22.
*Filament color.*—White.
*Anther color.*—Light brown.
*Attitude of styles.*—Semi-erect.
*Hair on ovary.*—Dense.
*Color of ovary.*—White.
*Number of sepals.*—6 to 7.
*Color of sepals.*—Near RHS Yellow-Green 144A.
*Sepal width.*—Approximately .7 cm.
*Sepal length.*—Approximately 1.1 cm.
*Sepal texture.*—Smooth.

Peduncle:
*Length.*—Average 6.4 cm.
*Color.*—Near RHS Yellow-Green 144C.
*Texture.*—Smooth.

FRUIT

*Color outer pericarp.*—Near RHS Yellow 1D.
*Color inner pericarp Near RHS Yellow* 3D.
*Core color.*—Near RHS White 155B.
*Brix at consumption.*—16.0–17.0.
*Brix at harvest.*—6.9%.
*Average weight.*—91 grams.
*Minimum weight.*—81 grams.
*Maximum weight.*—92 grams.
*Length.*—Avg. 58 mm.
*Width.*—Avg. 47 mm.
*Core diameter(maximum).*—15.6 mm.
*Core diameter(minimum).*—8.58 mm.
*Locule number.*—30.
*Fruit peduncle length.*—34 mm.
*Fruit peduncle width.*—3.2 mm.
*General shape.*—Oblong.
*Median cross section.*—Wide elliptic.
*Stylar end shape.*—Blunt protruding.
*Shoulder shape.*—Squared.
*Calyx ring.*—Present.
*Calyx ring expression.*—Moderate.
*Skin color at harvest.*—Near RHS Greyed-Orange 165D.
*Hair on fruit skin.*—Downy.
*Hair adherence to skin.*—Weak.
*Skin adherence to flesh at maturity.*—Moderate.
*Fruit core shape.*—Elliptic.
*Core-woody spike.*—Small.
*Lenticels on fruit.*—Not present.
*Mature seed color.*—Red/brown.
*Dried seed.*—Red/brown.
*Harvest time.*—Late March.
*Overall cropping quantity.*—Medium.

OTHER CHARACTERISTICS

Storage life: Storage life is a minimum of 3 months at 2° C.
Disease/pest resistance: Neither resistance nor susceptibility to pathogens and pests common to *Actinidia chinensis* have been observed.
Temperature tolerance: Tolerates low temperatures to approximately −8° C. without negative effects, tolerates high temperatures to approximately 35° C. without negative effects.

What is claimed is:

1. A new and distinct cultivar of *Actinidia chinensis* plant named 'X60' as herein illustrated and described.

* * * * *